United States Patent [19]

Haga et al.

[11] Patent Number: 4,727,077

[45] Date of Patent: Feb. 23, 1988

[54] BENZOYL UREA COMPOUNDS, PROCESS FOR THEIR PRODUCTION, AND ANTITUMOROUS COMPOSITIONS CONTAINING THEM

[75] Inventors: Takahiro Haga, Kusatsu; Nobutoshi Yamada, Moriyama; Hideo Sugi, Moriyama; Toru Koyanagi, Kyoto; Nobuo Kondo, Daito; Tsunetaka Nakajima, Kashiwara; Masahiro Watanabe, Akashi; Kazumasa Yokoyama, Toyonaka, all of Japan

[73] Assignee: Ishihara Sangyo Kaisha Ltd., Osaka, Japan

[21] Appl. No.: 823,521

[22] Filed: Jan. 29, 1986

[30] Foreign Application Priority Data

Feb. 20, 1985 [JP] Japan .................. 60-32365
Mar. 8, 1985 [JP] Japan .................. 60-44737

[51] Int. Cl.⁴ .................. C07D 251/22; A61K 31/53
[52] U.S. Cl. .................. 514/274; 544/316
[58] Field of Search .................. 544/316; 514/274

[56] References Cited

U.S. PATENT DOCUMENTS

B 435,617 3/1976 Johnston .................. 260/256.4

FOREIGN PATENT DOCUMENTS 0123861 11/1984 European Pat. Off. .
57-109721 7/1982 Japan .
795469 1/1981 U.S.S.R. .

OTHER PUBLICATIONS

Patent Abstracts of Japan, C Field, vol. 6, No. 202, Oct. 13, 1982 [Abstract of 57-109721 (A)], The Patent Office Japanese Government, p. 6 C 129 (Ishihara Sangyo K.K.).
Chemical Abstracts, vol. 98, p. 67 (1983); 98:101190r, Ishihara et al.
Russian Inventor's Certificate 1,235,864.

*Primary Examiner*—Joseph Paul Brust
*Attorney, Agent, or Firm*—Oblon, Fisher, Spivak, McClelland & Maier

[57] ABSTRACT

A benzoyl urea compound having the formula:

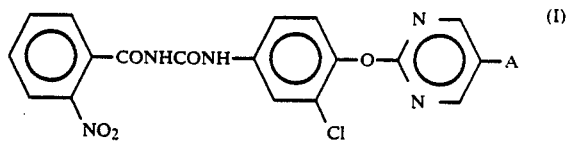

wherein A is a bromine atom or a chlorine atom.

10 Claims, No Drawings

BENZOYL UREA COMPOUNDS, PROCESS FOR THEIR PRODUCTION, AND ANTITUMOROUS COMPOSITIONS CONTAINING THEM

The present invention relates to novel benzoyl urea compounds, a process for their production, and antitumorous compositions containing them as active ingredients.

Heretofore, it has been disclosed that benzoyl urea compounds having the formula:

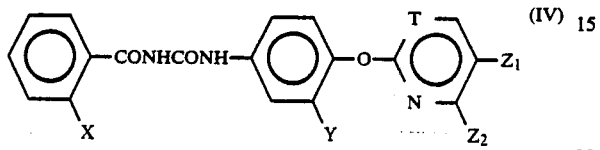

wherein X is a halogen atom or a nitro group, each of Y and $Z_2$ is a hydrogen atom or a halogen atom, $Z_1$ is a halogen atom or a trifluoromethyl group, and T is =CH— or =N—, are useful as antitumour drugs. More specifically, it has been disclosed that when cancer cells were intraperitoneally inoculated to mice, and the drugs were administered also intraperitoneally to the mice, antitumour effects were obtained (Japanese Unexamined Patent Publication No. 109721/1982).

However, these compounds are generally hardly soluble in both water and organic solvents, and accordingly poorly absorbable by the gut. Therefore, depending upon the manner of administration, they sometimes hardly exhibit antitumour activities, and there is a limitation for the intraperitoneal administration of such drugs for curing purposes. Accordingly, further improvements are desired so that these compounds may exhibit excellent antitumour effects without bringing about any side effects, by a practical and simple manner of administration in a practical and simple formulation for the purpose of curing cancer.

The object of the present invention is to provide novel benzoyl urea compounds which may be covered by the above general formula IV but not specifically disclosed in the above publication, a method for their production, and antitumorous compositions containing them as active ingredients.

Namely, according to the first aspect, the present invention provides a benzoyl urea compound having the formula:

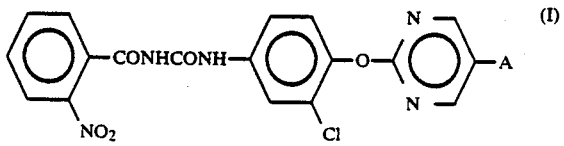

wherein A is a bromine atom or a chlorine atom.

According to the second aspect, the present invention provides a process for producing the above compound of the formula I by reacting a nitro-substituted benzene compound having the formula:

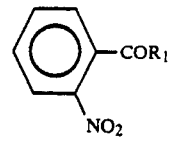

wherein $R_1$ is an isocyanate group, an amino group, or a

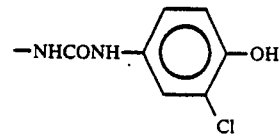

group, with a substituted pyrimidine compound having the formula:

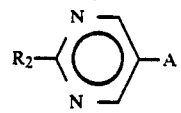

wherein A is as defined above, $R_2$ is a halogen atom, or a

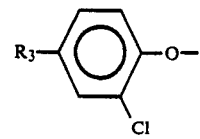

group wherein $R_3$ is an isocyanate group or an amino group which differs from $R_1$ with the proviso that when $R_1$ is an isocyanate group or an amino group, then $R_2$ is a

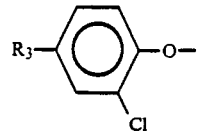

group, and when $R_1$ is a

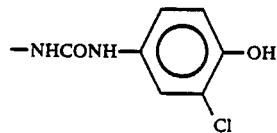

group, then $R_2$ is a halogen atom.

Further, according to the third aspect, the present invention provides an antitumorous composition containing a compound of the formula I as an active ingredient.

Firstly, the present inventors have conducted extensive researches on the compounds represented by the general formula IV and studied the chemical structures and the antitumour activities in detail, and as a result, they have found that desirable antitumour activities are obtainable in the case of a combination wherein, in the above formula IV, X is a nitro group, Y is a chlorine atom, T is =N—, $Z_1$ is a halogen atom, and $Z_2$ is a hydrogen atom. Then, in such a combination, a remarkable difference in the antitumour activities is observable due to the difference of the halogen atom as $Z_1$, when the portion to which the cancer cells are inoculated, and the portion to which the drug is administered, are different. Namely, as between the case wherein $Z_1$ is an chlorine atom or a bromine atom and the case wherein $Z_1$ is an iodine atom, substantially superior activities are observed in the former as compared with the latter when the above-mentioned portions are different, although there is no substantial difference in the antitumour activities when the above portions are the same. Namely, the present invention is based on the discovery that those compounds which are not disclosed in the above-mentioned publication have superior antitumour activities to those specifically mentioned in the publication.

The reason for the difference in the antitumour activities due to the difference of the halogen atom as $Z_1$, is not fully understood. However, it is considered that depending upon the manner of administration of the drugs, the absorption of the drugs by the gut, the concentration of the drugs in blood and the transfer property of the drug to the target portion, may vary depending upon the difference of the type of the halogen atom, whereby there may be a substantial difference in the arrival of the drugs to the diseased portion, and a substantial difference in the antitumour activities is thereby brought about. Thus, it appears that a certain specific property of the compounds of the present invention is somewhat related to the antitumour activities. According to the present invention, excellent antitumour activities can be obtained by a method for supplying the drug indirectly to the diseased portion, i.e. by a method of administration of the drug to the whole body in which the diseased portion is apart from the portion to which the drug is administered, such as oral administration, intravenous (intravenous injection) administration, suppository (rectal) administration, intramuscular administration, or percutaneous administration, preferably by the oral, intervenous or suppository administration, more preferably by the oral administration. Further, according to the present invention, the administration of the drug can be simplified, and as the amount of the drug can be reduced, there will be advantages such that the pain to the patient at the time of the administration can be reduced, and the side effects can be reduced.

The benzoyl urea compound of the present invention may be prepared, for instance, by the following processes.

[A]

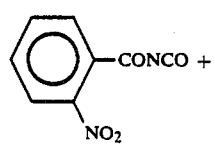

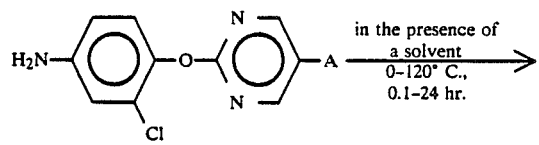

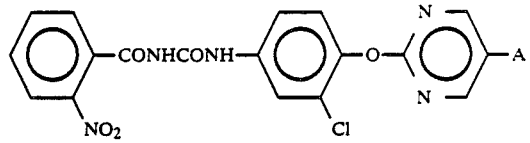

wherein A is as defined above.

As the solvent to be used in the above reaction, there may be mentioned octane, benzene, toluene, xylene, pyridine, dioxane, dimethylsulfoxide, monochlorobenzene or ethyl acetate.

[B]

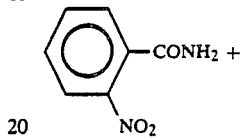

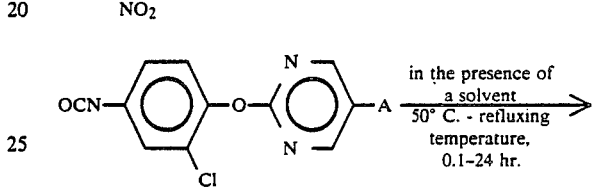

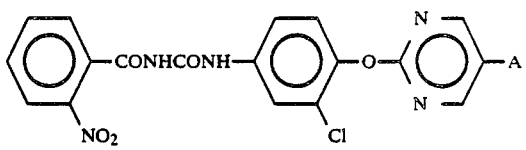

wherein A is as defined above.

The solvent to be used in the above reaction, is the same as one used in the reaction [A].

[C]

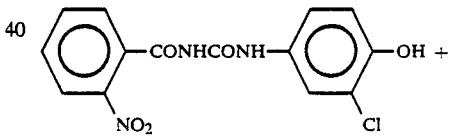

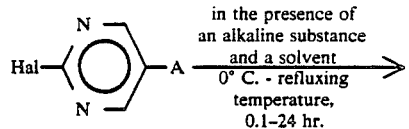

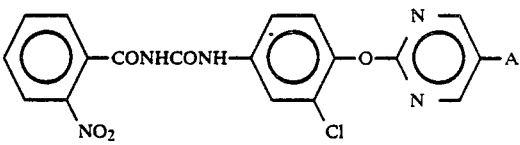

wherein Hal is a halogen atom and A is as defined above.

As the alkaline substance to be used in the above reaction, there may be mentioned sodium hydroxide, potassium hydroxide, sodium carbonate or potassium carbonate. As the solvent, there may be mentioned an aprotic polar solvent such as dimethylsulfoxide, dimethylformamide, hexamethylphosphoroamide and sulfolane, a ketone such as acetone, methyl ethyl ketone and methyl isobutyl ketone, and a halogenated hydrocarbon such as methylenechloride or chloroform.

The aniline compound, the phenyl isocyanate compound or the N-substituted phenyl-N'-benzoyl urea compound used as the starting material in each of the above reactions, is prepared, for instance, by the following processes.

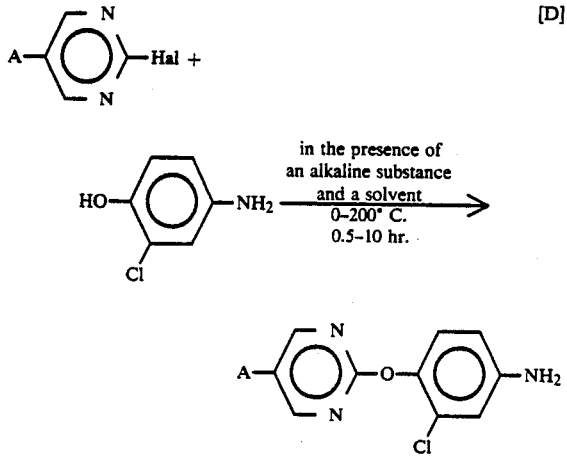

wherein Hal and A are as defined above.

The alkaline substance and solvent to be used are the same as ones used in the reaction [C]. Further, this condensation reaction is preferably conducted in the presence of nitrogen gas.

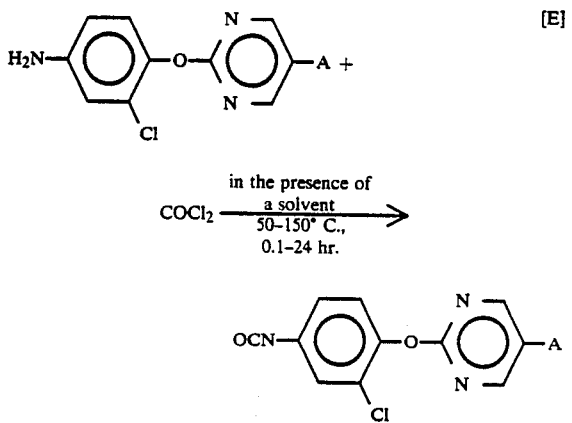

wherein A is as defined above.

As the solvent to be used, there may be mentioned a solvent inert to phosgene, such as toluene, xylene, monochlorobenzene, ethyl acetate or dioxane.

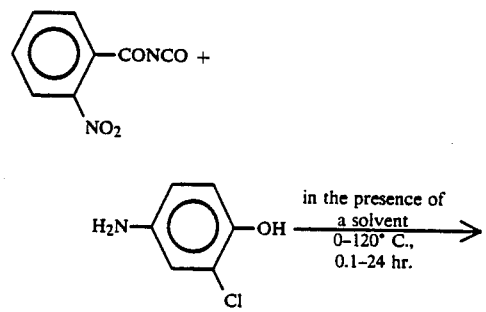

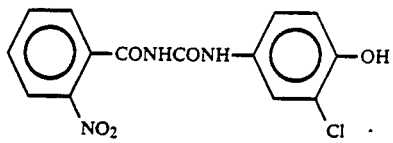

The solvent to be used in the above reaction, is the same as one used in the reaction [A].

Now, the present invention will be described in further detail with reference to Examples. However, it should be understood that the present invention is by no means restricted by these specific Examples.

SYNTHETIC EXAMPLE 1

Synthesis of Compound No. 1

N-(2-nitrobenzoyl)-N'-[4-(5-bromo-2-pyrimidinyloxy)-3-chlorophenyl]urea (1) Into a flask, 7.00 g of 5-bromo-2-chloropyrimidine, 5.19 g of 4-amino-2-chlorophenol, 9.98 g of potassium carbonate and 70 ml of dimethylsulfoxide were introduced, and reacted in a nitrogen atmosphere at 120° C. for 1.5 hours under stirring. After the completion of the reaction, the product was poured into water, and extracted with ethyl acetate. The extract was washed with water and a saturated sodium chloride aqueous solution, dried over anhydrous sodium sulfate, and then purified by silica gel column chromatography, whereby 6.80 g of oily 4-(5-bromo-2-pyrimidinyloxy)-3-chloroaniline was obtained.

(2) Into a flask, a solution obtained by dissolving 6.80 g of the above 4-(5-bromo-2-pyrimidinyloxy)-3-chloroaniline in 30 ml of dioxane, was introduced, and a solution obtained by dissolving 5.76 g of 2-nitrobenzoylisocyanate in 30 ml of dioxane, was dropwise added thereto, and then the mixture was reacted at room temperature for 9 hours. After the completion of the reaction, the product was poured into water, subjected to filtration and washed with hot water. The crystals thereby obtained were put into methanol, and stirred, and then subjected to filtration again, to obtain 9.42 g of the desired product having a melting point of from 234 to 236° C.

SYNTHETIC EXAMPLE 2

Synthesis of Compound No. 2:

N-(2-nitrobenzoyl)-N'-[3-chloro-4-(5-chloro-2-pyrimidinyloxy)phenyl]urea (1) Into a flask, 1.50 g of 2,5-dichloropyrimidine, 1.45 g of 4-amino-2-chlorophenol, 2.76 g of potassium carbonate and 15 ml of dimethylsulfoxide, were introduced, and reacted in a nitrogen atmosphere at 100° C. for 1.5 hours under stirring. After the completion of the reaction, the product was poured into water, and extracted with diethyl ether. The extract was washed with a saturated sodium chloride aqueous solution, and dried over anhydrous sodium sulfate, and then the solvent was distilled off. The crude product thereby obtained was purified and isolated by silica gel column chromatography to obtain 2.20 g of 3-chloro-4-(5-chloro-2-pyrimidinyloxy)aniline having a melting point of from 95 to 96° C.

(2) Into a flask, a solution obtained by dissolving 1.50 g of 2-nitrobenzoyl isocyanate in 6.5 ml of dioxane, was introduced, and a solution obtained by dissolving 1.00 g of the 3-chloro-4-(5-chloro-2-pyrimidinyloxy)aniline obtained in the above step in 6.5 ml of dioxane, was dropwise added thereto, and the mixture was reacted at room temperature for 3 hours. After the completion of the reaction, the product was poured into water, and the precipitated crystals were collected by filtration. These crystals were washed with water of about 50° C., dried, and suspended in ethyl acetate. A small amount of n-hexane was added thereto, and the precipitated crystals were collected by filtration, and dried to obtain 1.05 g of the desired product having a melting point of from 222 to 225° C.

SYNTHETIC EXAMPLE 3

Synthesis of Compound No. 1

(1) Into a flask, a solution of 0.02 mol of phosgene in 30 ml of ethyl acetate was introduced. To this solution, a solution of 3 g of 4-(5-bromo-2-pyrimidinyloxy)-3-chloroaniline in 10 ml of ethyl acetate was dropwise added at room temperature. The mixture was reacted at room temperature for 3 hours under stirring and further under reflux for one hour. After completion of the reaction, ethyl acetate was distilled off under reduced pressure, and the residue was vacuum-dried to obtain 3.10 g of 4-(5-bromo-2-pyrimidinyloxy)-3-chlorophenylisocyanate having a melting point of from 63 to 68° C. (2) Into a flask, 1.22 g of 4-(5-bromo-2-pyrimidinyloxy)-3-chlorophenylisocyanate obtained in the above step was introduced, and 20 ml of toluene was added thereto. Further, 0.62 g of 2-nitrobenzamide was added under stirring. The mixture was reacted under reflux for 4 hours. After completion of the reaction, 5 ml of methanol was added to the reaction product, and the mixture was cooled. The precipitated crystals were collected by filtration to obtain 0.79 g of the desired product.

SYNTHETIC EXAMPLE 4

Synthesis of Compound No. 1 (1) Into a flask, a solution of 5.19 g of 4-amino-2chlorophenol in 100 ml of dioxane was introduced. To this solution, a solution of 5.78 g of 2-nitrobenzoylisocyanate in 10 ml of dioxane was dropwise added at room temperature. The mixture was reacted at room temperature for 12 hours under stirring. After completion of the reaction, the reaction product was introduced into water. The precipitated crystals were collected by filtration, and washed with methanol to obtain 8.60 g of N-(2-nitrobenzoyl)-N'-(3-chloro-4-hydroxyphenyl)urea having a melting point of from 237° to 239° C.

(2) Into a flask, a solution of 1 g of N-(2-nitrobenzoyl)N'-(3-chloro-4-hydroxyphenyl)urea obtained in the above step in 10 ml of dimethylsulfoxide, was introduced, and 0.14 g of potassium hydroxide and then 0.58 g of 5-bromo-2-chloropyrimidine were added thereto. The mixture was reacted at 50° C. for 5 hours. After completion of the reaction, 20 ml of methanol was added to the reaction product. The precipitated crystals were collected by filtration. These crystals were washed with water and methanol to obtain 0.81 g of the desired product.

Specific compounds of the present invention are listed below.

20 Compound No. 1

N-(2-nitrobenzoyl)-N'-[3-chloro-4-(5-bromo-2-pyrimidinyloxy)phenyl]urea.
Melting point: 234°-236° C.

Compound No. 2

N-(2-nitrobenzoyl)-N'-[3-chloro-4-(5-chloro-2pyrimidinyloxy)phenyl]urea. Melting point: 222°-225° C.

Specific intermediates of the present invention will be listed below.

4-(5-bromo-2-pyrimidinyloxy)-3-chloroaniline. Melting point: 52°-61.5° C.

3-chloro-4-(5-chloro-2-pyrimidinyloxy)aniline. Melting point: 95°-96° C.

4-(5-bromo-2-pyrimidinyloxy)-3-chlorophenyl isocyanate. Melting point: 63°-68° C.

N-(3-chloro-4-hydroxyphenyl)-N'-(2-nitrobenzoyl)urea Melting point: 237°-239° C.

Now, the names of the comparative compounds used in the following examples will be given.

Comparative Compound No. 1

N-(2-nitrobenzoyl)-N'-[3-chloro-4-(5-iodo-2-pyrimidinyloxy)phenyl]urea. (disclosed in Japanese Unexamined Patent Publication No. 109721/1982)

Now, the peculiar antitumour activities of the benzoyl urea compounds of the present invention will be shown.

For instance, as compared with Comparative Compound No. 1, the name and the antitumour effects of which are specifically disclosed in the above publication, Compound Nos. 1 and 2 of the present invention show no substantial superiority in the antitumour activities in the case of Test Example 1 (wherein the portion to which cancer cells were inoculated and the portion to which the drug was administered, were the same), but they show extremely superior activities in the case of Test Examples 2 and 3 (wherein the above-mentioned two portions were different).

TEST EXAMPLE 1

(The inoculation of the cancer cells and the administration of the drug were both made intraperitoneally, as in the case of Test Example 1 of the above publication.)

To $BDF_1$ mice, p-388 leukemia cells were intraperitoneally inoculated in an amount of $1 \times 10^6$ cells/mouse. A test drug was intraperitoneally administered twice, i.e. one day and four days after the inoculation. The mice were observed for 30 days for survival or death. The ratio (%) of median survival time (MST) of test and control animals was obtained with the number of survival days of mice of the control group to which a physiological saline was administered, being evaluated as 100. The drug was a dispersion obtained by adding a small amount of a surfactant (e.g. Tween-80, manufactured by Atlas Powder Co.) to the test compound (Table 1).

TABLE 1

| Compound No. | Dose (Active ingredient mg/kg/day) | T/C (%) of MST |
|---|---|---|
| 1 | 25 | 168 |
|  | 12.5 | 173 |
| 2 | 25 | 210 |
|  | 12.5 | 150 |
| Comparative | 25 | 230 |
| Compound No. 1 | 12.5 | 171 |

TEST EXAMPLE 2

(The p-388 leukemia cells were inoculated intraperitoneally, while the drug was administered orally.)

To BDF$_1$ mice, p-388 leukemia cells were intraperitoneally inoculated in an amount of $1 \times 10^6$ cells/mouse. A test drug was orally administered twice, i.e. one day and four days after the inoculation. The mice were observed for 30 days for survival or death, and the ratio (%) of median survival time of test and control animals was obtained with respect to each treated group (10 animals per group) with the number of survival days of mice of the control group to which a physiological saline was administered, being evaluated as 100 (Table 2).

The test drugs were formulated in accordance with Formulation Example 1 given hereinafter.

TABLE 2

| Compound No. | Dose (Active ingredient mg/kg/day) | T/C (%) of MST[1] |
|---|---|---|
| 1 | 100 | 173 |
|  | 50 | 157 |
| 2 | 50 | 178 |
|  | 25 | 139 |
| Comparative Compound No. 1 | 1600 | 186 |
|  | 800 | 143 |
|  | 400 | 116 |

TEST EXAMPLE 3

(The p-388 leukemia cells were inoculated intraperitoneally, whereas the drug was administered orally.)

The ratio (%) of median survival time of test and control animals, was determined in the same manner as in Test Example 2 except that the test drugs formulated in accordance with Formulation Example 1 were replaced by the test drugs formulated in accordance with Formulation Example 2 (Table 3).

TABLE 3

| Compound No. | Dose (Active ingredient mg/kg/day) | T/C (%) of MST |
|---|---|---|
| 1 | 400 | 235 |
|  | 300 | 180 |
|  | 200 | 143 |
| Comparative Compound No. 1 | 3200 | 183 |
|  | 1600 | 141 |

TEST EXAMPLE 4

(The L-1210 leukemia cell was inoculated intraperitoneally, whereas the drug was administered intravenously.)

To BDF$_1$ mice, L-1210 leukemia cells were intraperitoneally inoculated in an amount of $1 \times 10^5$ cells/mouse. A test drug formulated in accordance with Formulation Example 2, was intravenously administered. The mice were observed for 30 days for survival or death, and the ratio (%) of median survival time of test and control animals was obtained with respect to each treated group (10 animals per group) with the number of survival days of mice of the control group to which a physiological saline was administered, being evaluated as 100 (Table 4).

TABLE 4

| Compound No. | Dose (Active ingredient mg/kg/day) | T/C (%) of MST |
|---|---|---|
| 1 | 12.5 | 195 |

TEST EXAMPLE 5

(The L-1210 leukemia cells were inoculated intraperitoneally, whereas the drug was administered orally.)

To BDF$_1$ mice, L-1210 leukemia cells were intraperitoneally inoculated in an amount of $1 \times 10^5$ cells/mouse. A test drug formulated in accordance with Formulation Example 1, was orally administered twice, i.e. one day and four days after the inoculation. The mice were observed for 30 days for survival or death, and the ratio (%) of median survival time of test and control animals was obtained with respect to each treated group (10 animals per group) with the number of survival days of mice of the control group to which a physiological saline was administered, being evaluated as 100 (Table 5).

TABLE 5

| Compound No. | Dose (Active ingredient mg/kg/day) | T/C (%) of MST |
|---|---|---|
| 1 | 100 | 213 |
|  | 50 | 165 |

TEST EXAMPLE 6

(The B-16 melanoma cell was inoculated intraperitoneally, whereas the drug was administered orally.)

To BDF$_1$ mice, 0.5 ml of liquid obtained by dispersing 1 g of B-16 melanoma cell in 8 cc of physiological saline was intraperitoneally inoculated in an amount of 0.5 ml/mouse. A test drug formulated in accordance with Formulation Example 1, was orally administered three times, i.e. one day, seven days and fourteen days after inoculation. The mice were observed for 60 days for survival or death, and the ratio (%) of median survival time of test and control animals was obtained with respect to each treated group (10 animals per group) with the number of survival days of mice of the control group to which a physiological saline was administered, being evaluated as 100 (Table 6).

TABLE 6

| Compound No. | Dose (Active ingredient mg/kg/day) | T/C (%) of MST |
|---|---|---|
| 1 | 100 | 139 |

TEST EXAMPLE 7

(The M-5074 ovarium sarcoma cells were inoculated intraperitoneally, whereas the drug was administered orally.)

To BCF$_1$ mice, M-5074 ovarium sarcoma cells were intraperitoneally inoculated in an amount of $1 \times 10^6$ cells/mouse. A test drug formulated in accordance with Formulation Example 1, was orally administered three times, i.e. one day, seven days and fourteen days after inoculation. The mice were observed for 60 days for survival or death, and the ratio (%) of median survival time of test and control animals was obtained with respect to each treated group (10 animals per group) with the number of survival days of mice of the control group to which a physiological saline was administered, being evaluated as 100 (Table 7).

TABLE 7

| Compound No. | Dose (Active ingredient mg/kg/day) | T/C (%) of MST |
| --- | --- | --- |
| 1 | 25 | 139 |

Now, the acute toxicity, doses and administration routes of the benzoyl urea compounds of the present invention will be described.

(1) Acute toxicity:

To ddY mice (10 animals), a drug containing Compound No. 1 or No. 2 of the present invention formulated in accordance with Formulation Example 1 was intravenously administered in an amount of the compound of 100 mg/kg, whereupon no mice died. Thus, the acute toxicity values ($LD_{50}$) of Compounds No. 1 and No. 2 were found to be at least 100 mg/kg.

(2) Doses

As to the dose, said compounds are administered continuously or intermittently in a range in which the total dose does not exceed a certain level, in consideration of the results of animal experiments and various conditions. However, the dose may, of course, be properly varied depending on the administration route, and on the conditions of a patient or an animal to be treated (for example, age, body weight, sex, sensitivity, food and the like), interval of administration, drugs used in combination with said compounds and the degree of disease. An optimum dose and the number of administrations under certain conditions should be determined by medical specialists.

(3) Administration routes

The antitumour drugs of the present invention may be administered through oral, intravenous, rectal, intramuscular and subcutaneous routes, preferably through oral, intravenous or rectal routes, more preferably through an oral route. In such a case, the compounds of the present invention may be formulated by using various pharmacologically acceptable carriers such as inert diluents or anaboilic food carriers as in the case of ordinary medicines, and preferably administered orally, intravenously or by suppository administration, particularly preferably by oral administration.

The compounds of the present invention are hardly soluble in both water and organic solvents. Therefore, they are preferably formulated into an aqueous suspension which may further contain phospholipids. As a method for producing an aqueous suspension containing no phospholipids, there may be mentioned a method wherein the active compound is preliminarily pulverized into fine powder, then the fine powder of the active compound is added to an aqueous solution containing a surfactant and, if necessary, a defoaming agent, the mixture is pulverized in a wet system until 80% of particles have a particle size of not higher than 5 $\mu$m, more preferably not higher than 2 $\mu$m, and, if necessary a thickener is added thereto. As specific examples of the surfactant, there may be mentioned a non-ionic phosphoric acid ester, a polyoxyethylene hardened castor oil, a polyoxyethylene sorbitan fatty acid ester, a sugar ester, a polyoxyethylene polyoxypropylene block polymer, etc. As specific examples of the defoaming agent, there may be mentioned dimethylpolysiloxane, methylphenylsiloxane, a sorbitan fatty acid ester, a polyoxyethylene-polyoxypropylene cetyl ether, silicone, etc. As specific examples of the thickener, there may be mentioned guar gum, alginic acid, gum arabic, pectin, starch, xanthane gum, gelatin, etc.

On the other hand, as a method for preparing an aqueous suspension containing a phospholipid, there may be mentioned a method wherein a phospholipid such as soybean phospholipid or yolk phospholipid is used instead of the surfactant in the above-mentioned method, and an antioxidant such as $\alpha$-tocopherol is used instead of the thickener.

Further, as another method for the preparation of an aqueous suspension containing a phospholipid, there may be mentioned the following method. A phospholipid and a compound of the present invention are dissolved in an organic solvent such as chloroform, and, if necessary, an antioxidant is added. Then, the solvent is distilled off under reduced pressure so as to deposit a thin layer of the phospholipid on the inner wall of the container to obtain a thin layer of the phospholipid containing the compound of the present invention. Then, a physiologically acceptable aqueous solution is added to the thin layer thus formed, followed by shaking or stirring to destroy the thin layer, and the suspension thereby obtained is subjected to supersonic treatment and centrifugal separation, whereby the obtained residue of the lower most layer is recovered and centrifugally washed with an aqueous solution containing a phospholipid (particle size: at most 5 $\mu$m, e.g. from 0.2 to 2 $\mu$m).

Further, these compounds may be formulated into tablets, capsules, enteric agents, granules, powders, injection solution or suppositories by common methods for formulations.

Now, specific formulation examples will be described.

FORMULATION EXAMPLE 1

The Compound No. 1 of the present invention was preliminarily pulverized by a centrifugal pulverizer. On the other hand, 5 parts by weight of polyoxyethylene (60) hardened castor oil, 0.2 part by weight of silicone and 0.3 part by weight of a polyoxyethylene-polyoxypropylene block polymer, were added to 79.5 parts by weight of a physiological saline to obtain an aqueous solution, to which 10 parts by weight of the above pulverized Compound No. 1 of the present invention was added. The mixture was pulverized in a wet system by a sand mill using glass beads (80% of particles having a particle size of not larger than 2 $\mu$m). Then, 5 parts by weight of xanthane gum (2% solution) was added thereto to obtain an aqueous suspension.

FORMULATION EXAMPLE 2

0.24 Parts by weight of Compound No. 1 of the present invention, 2.4 parts by weight of purified yolk phospholipid and 0.0024 part by weight of $\alpha$-tocopherol were dissolved in 48.7576 parts by weight of chloroform, and then chloroform was distilled off by heating under reduced pressure by means of a rotary evaporator, to form a thin layer of a phospholipid containing Compound No. 1 of the present invention. To this thin layer, 48.6 parts by weight of a physiological sodium chloride aqueous solution was added, and immediately vigorously shaked at room temperature, and then supersonic treatment was conducted for 1 hour under cooling with ice by means of a Sonycator. Further, centrifugal separation was conducted at room temperature, whereupon the residue at the lower most layer was recovered, and centrifugally washed a few times with the above-mentioned physiological sodium chloride aqueous solution, and then filtered for the removal of bacteria, whereby an aqueous suspension containing phospholipid (particle size: 0.2–2 μm) was obtained.

FORMULATION EXAMPLE 3

The aqueous suspension obtained in Formulation Example 2 was freeze-dried to obtain a dry formulation containing a phospholipid.

As described in detail in the foregoing, the present invention provides compounds which exhibit extremely superior antitumour activities even when an administration method is employed wherein the portion to which the drug is administered is apart from the diseased portion. Further, according to the present invention, the administration can be simplified, and the dose can be reduced, whereby the pain to the patient at the time of the administration and the side effects can be reduced.

FORMULATION EXAMPLE 4

To an aqueous solution obtained by dissolving 1.5 parts by weight of oxyethylated polyallylphenol phosphate and 0.2 part by weight of silicone in 53.3 parts by weight of a physiological saline, 40 parts by weight of Compounds No. 2 of the present invention puverlized by a centrifugal pulverizer, was added, and the mixture was pulverized in a wet system in the sand mill by using glass beads (90% of particles having a particle size of not larger than 2 μm). Then, 5 parts by weight of xanthane gum (2% solution) was added thereto to obtain an aqueous suspension.

FORMULATION EXAMPLE 5

Compounds No. 1 of the present invention was preliminarily pulverized by a centrifugal pulverizer. 5 parts by weight of pulverized Compound No. 1 of the present invention was added to an aqueous solution obtained by stirring and dispersing 2 parts by weight of yolk phospholipid, 0.001 part by weight of α-tocopherol and 92.999 parts by weight of a physiological saline. Then, the mixture was pulverized in a wet system in a sand mill by using glass beads (80% of particles having particle size of not larger than 2 μm) to obtain an aqueous suspension.

We claim:

1. A benzoyl urea compound having the formula:

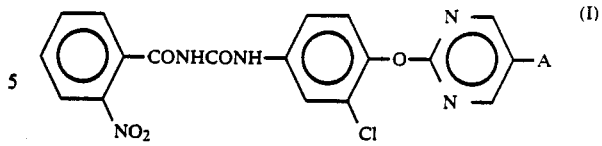

wherein A is a bromine atom or a chlorine atom.

2. The benzoyl urea compound according to claim 1, which is N-(2-nitrobenzoyl)-N'-[4-(5-bromo-2-pyrimidinyloxy)-3-chlorophenyl]urea.

3. The benzoyl urea compound according to claim 1, which is N-(2-nitrobenzoyl)-N'-[3-chloro-4-(5-chloro-2-pyrimidinyloxy)phenyl]urea.

4. An antitumorous composition comprising:
an antitumorously effective amount of a benzoyl urea compound having the formula:

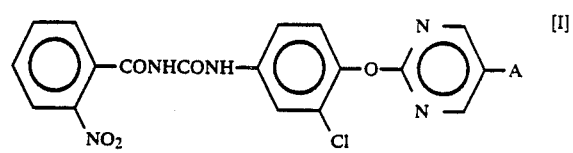

where A is a bromine atom or a chlorine atom and a pharmaceutically acceptable adjuvant.

5. The antitumorous composition according to claim 4, wherein the pharmaceutically acceptable adjuvant is a surfactant.

6. The antitumorous composition according to claim 4, wherein the pharmaceutically acceptable adjuvant is a phospholipid and an antioxidant.

7. The antitumorous composition according to claim 4, wherein at least 80% of the benzoyl urea compound has a particle size of not larger than 5 μm.

8. The antitumorous composition according to claim 4, which is applied for oral administration, intravenous administration or suppository administration.

9. The antitumorous composition according to claim 4, which is applied for oral administration.

10. A method of treating a cancer resulting from the growth of P-388 leukemia cells, L-1210 leukemia cells, B-16 melanoma cells and M-5074 ovarium sarcoma cells, comprising:
administering to a host subject suffering from said cancer an antitumorously effective amount of a benzoyl urea compound of the formula:

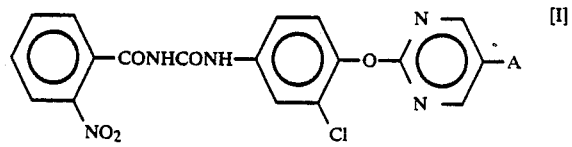

wherein A is bromine or chlorine.

* * * * *